US00PP28961P2

(12) United States Plant Patent
Berry

(10) Patent No.: US PP28,961 P2
(45) Date of Patent: Feb. 13, 2018

(54) ***GARDENIA* PLANT NAMED 'PS-2013-3'**

(50) Latin Name: *Gardenia jasminoides*
Varietal Denomination: PS-2013-3

(71) Applicant: Capstone Plants Inc., Grand Saline, TX (US)

(72) Inventor: James B. Berry, Edgewood, TX (US)

(73) Assignee: CAPSTONE PLANTS, INC., Grand Saline, TX (US)

( * ) Notice: Subject to any disclaimer, the term of this patent is extended or adjusted under 35 U.S.C. 154(b) by 0 days.

(21) Appl. No.: 14/999,967

(22) Filed: Jul. 20, 2016

(51) Int. Cl.
*A01H 5/02* (2006.01)

(52) U.S. Cl.
USPC ..... Plt./255

(58) Field of Classification Search
USPC ..... Plt./255
See application file for complete search history.

*Primary Examiner* — Anne M Grunberg
(74) *Attorney, Agent, or Firm* — Penny J. Aguirre

(57) ABSTRACT

A new cultivar of *Gardenia* named 'PS-2013-3' that is characterized by its compact plant habit that is equal in height and width, its dense self-branching plant habit without pruning its large single flowers that bloom in late spring with two full spring cycles under ideal conditions followed by spot blooming through the fall, its glossy dark green foliage, its cold hardiness at least to U.S.D.A. Zone 7 with no winter foliage freezing, and its good resistance to root rot.

2 Drawing Sheets

Botanical classification: *Gardenia jasminoides.*
Variety denomination: 'PS-2013-3'.

BACKGROUND OF THE INVENTION

The present invention relates to a new and distinct cultivar of *Gardenia jasminoides*. The new cultivar will be referred to hereafter by its cultivar name, 'PS-2013-3'. 'PS-2013-3' is a new cultivar of *Gardenia* grown for use as a landscape shrub.

The new cultivar of *Gardenia* is a selection from a controlled breeding program conducted by the Inventor in Grand Saline, Tex. The objectives of the breeding program are to create new jasmine cultivars with good cold hardiness, floriferous blooming habits, glossy green foliage, and compact plant habits.

'PS-2013-3' originated from open pollination of *Gardenia jasminoides* 'Kleim's Hardy' (not patented) in May of 2011. The male parentage is therefore unknown. 'PS-2013-3' was selected as a single unique plant in May of 2013 from amongst the resulting seedlings.

Asexual propagation of the new cultivar was first accomplished by semi-hardwood stem cuttings under the direction of the Inventor in Grand Saline, Tex. in July of 2013. Asexual propagation by semi-hardwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'PS-2013-3' as a new and unique cultivar of *Gardenia.*

1. 'PS-2013-3' exhibits a compact plant habit that is equal in height and width.

2. 'PS-2013-3' exhibits a dense self-branching plant habit without pruning.
3. 'PS-2013-3' exhibits large single flowers that bloom in late spring with two full spring cycles under ideal conditions followed by spot blooming through the fall.
4. 'PS-2013-3' exhibits glossy dark green foliage.
5. 'PS-2013-3' exhibits cold hardiness at least to U.S.D.A. Zone 7 with no winter foliage freezing.
6. 'PS-2013-3' exhibits good resistance to root rot.

The female parent of 'PS-2013-3' differs from 'PS-2013-3' in having wider leaves, in having longer internodes, and in having a less dense, more open plant habit. 'PS-2013-3' can be most closely compared to the *Gardenia jasminoides* cultivars 'Whispering Pines' (not patented) and 'Double Mist' (U.S. Plant Pat. No. 23,507). 'Whispering Pines' is similar to 'PS-2013-3' in being resistant to root rot, and in having a bloom season that begins in the spring followed by spot blooming through the fall. 'Whispering Pines' differs from 'PS-2013-3' in having wider leaves, in having longer internodes, in having double flowers, and in having an open growth habit that is not self-branching. 'Double Mint' is similar to 'PS-2013-3' in having a long bloom season and in having a plant habit that is equal in height and width. 'Double Mint' differs from 'PS-2013-3' in having leaves that are shorter in length, in having leaves with more rounded apices, in having double flowers, in having leaves with less pronounced veins, and in having dull green foliage.

BRIEF DESCRIPTION OF THE DRAWINGS

The accompanying colored photographs illustrate the overall appearance and distinct characteristics of the new *Gardenia*. The photographs were taken of a 1 year-old plant as grown outdoors in a two-gallon container in Grand Saline, Tex.

The photograph in FIG. 1 provides a side view of the plant habit of 'PS-2013-3' in bloom.

Figure 1:
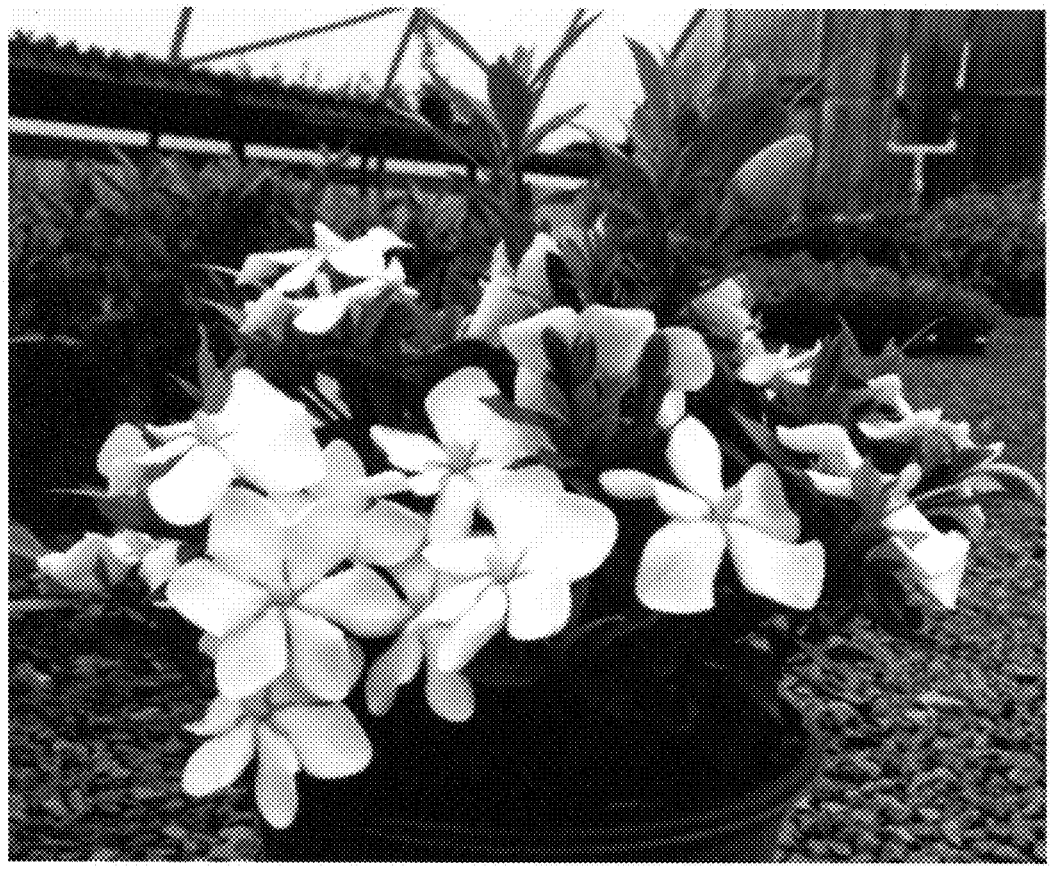
Figure 2:
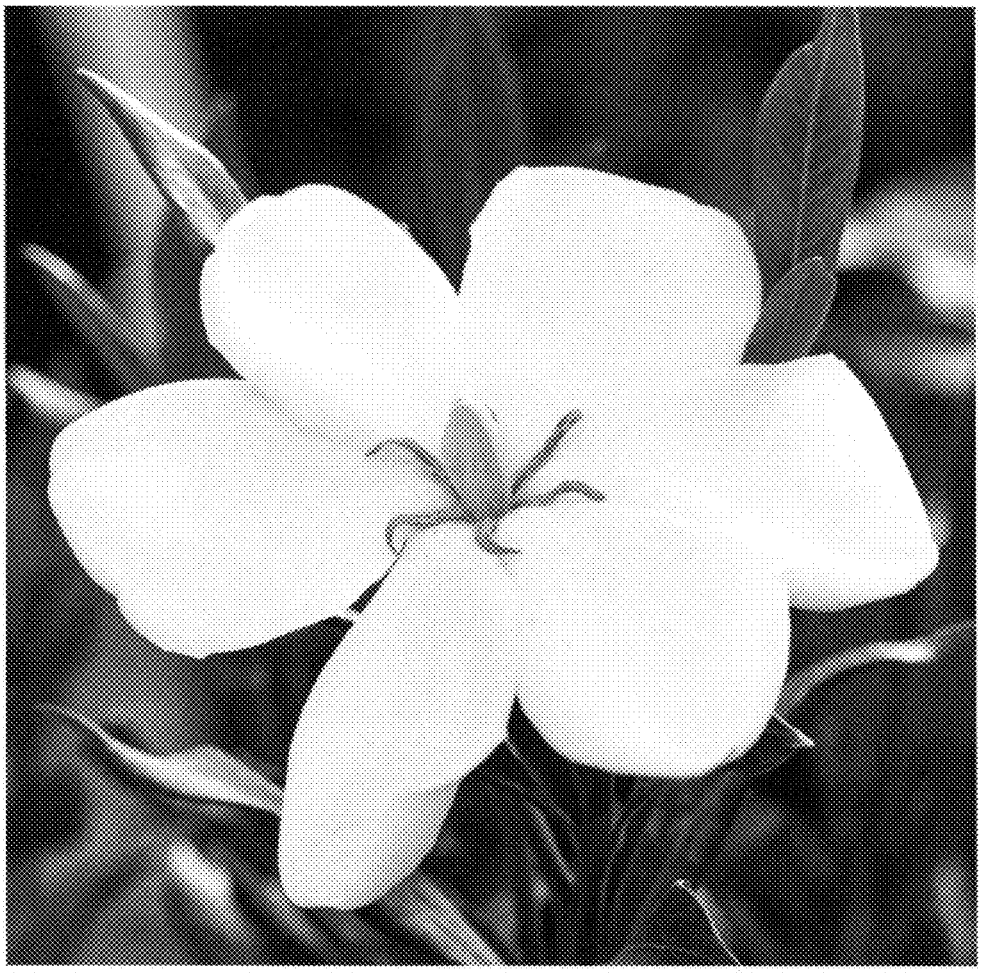

The photograph in FIG. 2 provides a close-up view of a flower of 'PS-2013-3'.

The colors in the photographs are as close as possible with the photographic and printing technology utilized and the color values cited in the detailed botanical description accurately describe the colors of the new *Gardenia*.

DETAILED BOTANICAL DESCRIPTION

The following is a detailed description of 1 year-old plants of the new cultivar as grown outdoors in two-gallon containers in Grand Saline, Tex. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming habit*.—Four weeks in mid spring (with two full spring cycles under ideal conditions) followed by spot flowering through fall in Grand Saline, Tex.

*Plant type*.—Evergreen shrub.

*Plant habit*.—Compact and very densely branched.

*Height and spread*.—An average of 91 cm in height and width as a mature plant in the landscape.

*Cold hardiness*.—At least to U.S.D.A. Zone 7.

*Diseases and pests*.—Good resistance to root rot (*Phytophthora* spp) has been observed.

*Propagation*.—Semi-hardwood stem cuttings.

*Growth rate*.—Vigorous.

*Root description*.—Fibrous roots, 160A to 165A in color.

*Root development*.—About 7 weeks to root and 18 months to finish in a 3-gallon container.

Branch description:

*Stem color*.—Young; 138A, maturing; 138A with woody striations of 199A and 165A, mature wood (at base); 199A and 165A.

*Stem surface*.—Young; glabrous, maturing; striated with woody streaks, mature wood; moderately coarse bark.

*Branching*.—5 lateral branches emerging from base, an average of 4 secondary branches per lateral branch.

*Internode length*.—Variable, up to 4.5 cm.

*Stem size*.—Lateral branches; an average of 17 cm in length and 5 mm in width, secondary branches; up to 11 cm in length and 3 mm in width.

*Stipules*.—Broadly elliptic in shape, 2 fused into sheath above leaf attachment, base truncate, an average of 8 3 mm in length and width, membranous surface, color 165A and somewhat translucent.

Foliage description:

*Leaf type*.—Simple.

*Leaf shape*.—Obovate.

*Leaf apex*.—Acuminate.

*Leaf base*.—Attenuate.

*Leaf arrangement*.—Whorls.

*Leaf venation*.—Pinnate, not conspicuous, color matches leaf coloration on upper and lower surface.

*Leaf fragrance*.—None.

*Leaf color*.—Young upper and lower surface; 143B, mature upper surface; 137A, mature lower surface; 148B.

*Leaf number*.—An average of 14 per lateral branch.

*Leaf surface*.—Shiny and glabrous on upper surface and glabrous and dull on lower surface.

*Leaf substance*.—Thick.

*Petioles*.—Short, an average of 3 mm in length and 2 mm in diameter, color 144A, surface glabrous and shiny.

Inflorescence description:

*Inflorescence type*.—Solitary from upper leaf axils.

*Flower number*.—An average of 3 to 4 per lateral branch (in different stages of opening).

*Flower fragrance*.—Strong, pleasant fragrance typical of *Gardenia*.

*Flower longevity*.—An average of 4 to 5 days, depending on temperature.

*Flower type*.—Salviform with lobes rotate.

*Flower size*.—An average of 5.5 cm in diameter and 4 cm in depth.

*Flower buds*.—Conical in shape, an average of 4 cm in length and 1.5 cm in width prior to opening, color 155C with sepal portion a blend of 138A and 138B, glabrous surface.

*Corolla lobes*.—An average of 6 per flower, arranged in a single whorl, slightly overlapping at base, primarily obovate in shape, an average of 2.6 cm in length and 2 cm in width, rounded to broadly acute apex, margins entire, base cuneate and fused into the corolla tube, aspect is primarily horizontal and slightly wavy, upper and lower surface is satiny, smooth and velvety, color upper surface when opening and fully open155C, color lower surface when opening and fully open 155C blended with areas of 2D, fading to a blend of 11B and 11C on both surfaces.

*Corolla tube*.—An average of 2.2 cm in length and 5 mm in width, surface texture of outer surfaces are glabrous, satiny and slightly ribbed, surface texture of inner surface is pubescent, color of inside and outside surface is 145B to 145C in color.

*Calyx*.—An average of 2.3 cm in length and 1.3 cm in diameter, campanulate with free lobes held early upright.

*Sepals*.—6, 60% un-fused from the calyx, glossy and glabrous on inner and outer surfaces, 2.3 cm in length with free lobes; 1.5 cm in in length, 2 mm in width, and lanceolate in shape, a blend of 138A and 138B in color on inner and outer surface.

*Peduncles*.—Oval in shape, average of 5 mm in length and 3 mm in diameter, glossy and glabrous surface, 138A in color.

Reproductive organs:

*Gynoecium*.—1 pistil, stigma; prominent and elliptic-obovate in shape, 3A in color, style; an average of 2 cm in length and 2 mm in diameter, 4D in color, ovary; 2-carpellate, 5 mm in length and 2 mm in width, oblong in shape, 4C in color, numerous shiny ovules.

*Androecium*.—An average of 6 stamens, filaments are adnate to inner corolla tube and 145D in color, anthers; alternate to petal lobes, an average of 1.1 cm in length and 1 mm in width, 177D in color, pollen is abundant and 3A in color.

*Fruit and seed*.—None observed to date.

It is claimed:

1. A new and distinct cultivar of *Gardenia* plant named 'PS-2013-3' as herein illustrated and described.

* * * * *